United States Patent [19]

Sims et al.

[11] Patent Number: 4,945,592
[45] Date of Patent: Aug. 7, 1990

[54] TRANSPORT SYSTEM FOR PORTABLE PATIENT CARE APPARATUS

[75] Inventors: Nathaniel M. Sims, Wellesley Hills; James P. Welch, Beverly, both of Mass.

[73] Assignee: The General Hospital Corporation, Boston, Mass.

[21] Appl. No.: 252,164

[22] Filed: Sep. 30, 1988

[51] Int. Cl.⁵ ............................................. A47C 21/00
[52] U.S. Cl. ...................................... 5/508; 248/129; 280/292; 5/503
[58] Field of Search .................. 5/508, 503, 504, 505; 108/8; 248/121, 129, 125, 229; 280/304.1, 478.1, 292

[56] References Cited

U.S. PATENT DOCUMENTS

| | | | |
|---|---|---|---|
| 2,696,963 | 12/1954 | Shepherd | 248/229 |
| 3,552,577 | 1/1971 | Latham | 211/74 |
| 3,709,372 | 1/1973 | Alexander | 5/503 |
| 3,709,556 | 1/1973 | Allard et al. | 248/125 |
| 4,511,157 | 4/1985 | Wilt | 280/289 WC |
| 4,511,158 | 4/1985 | Varga et al. | 280/292 |
| 4,600,209 | 7/1986 | Kerr | 280/400 |
| 4,725,027 | 2/1988 | Bekanich | 248/125 |
| 4,767,131 | 8/1988 | Springer et al. | 280/304.1 |
| 4,795,122 | 1/1989 | Petre | 248/317 |
| 4,824,132 | 4/1989 | Moore | 280/304.1 |

FOREIGN PATENT DOCUMENTS

| | | | |
|---|---|---|---|
| 1208680 | 2/1960 | France | 108/8 |
| 1476061 | 6/1977 | United Kingdom | 5/508 |

Primary Examiner—Eric K. Nicholson
Attorney, Agent, or Firm—Lahive & Cockfield

[57] ABSTRACT

An apparatus for transporting a patient care device comprises a vertically adjustable first horizontal flange secured to a patient transport device, a patient care apparatus having an elongate vertical member supporting a patient care device, and a second horizontal flange disposed on an upper portion of the vertical member of the patient care apparatus. The upper portion of the vertical member may be detachable from the base portion thereof. In order to secure the patient care device to the patient transport apparatus, a mating means on the first horizontal flange is aligned directly below a mating means on the second horizontal flange. The first horizontal flange is then elevated until it interlockingly engages the second horizontal flange. The first flange is further elevated until the upper portion of the vertical member detaches from the base portion and becomes freely supported by the patient transport device.

20 Claims, 2 Drawing Sheets

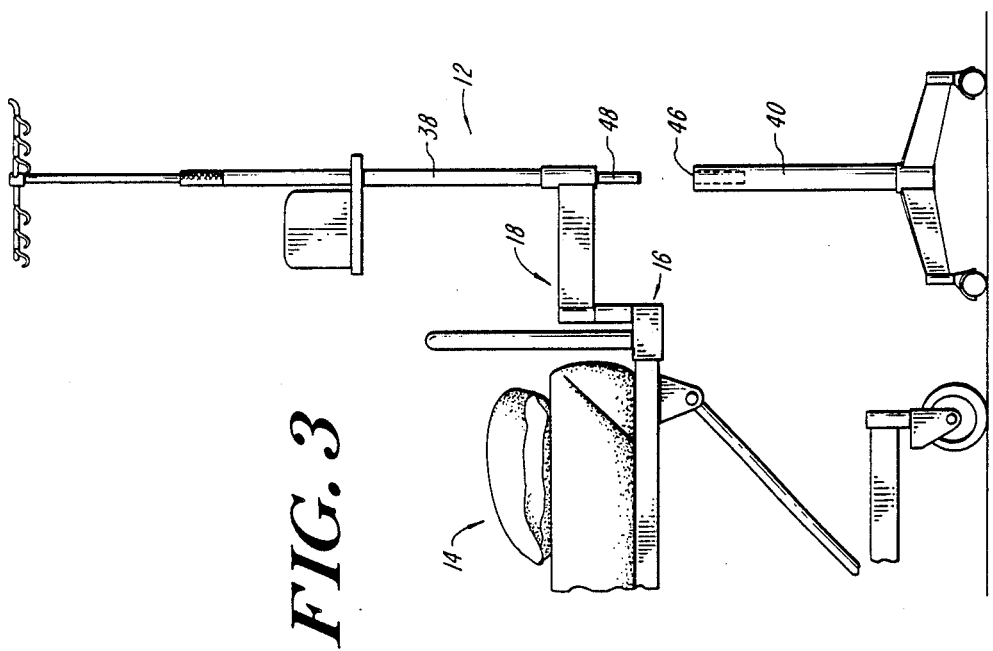

TRANSPORT SYSTEM FOR PORTABLE PATIENT CARE APPARATUS

BACKGROUND OF THE INVENTION

The present invention relates to an apparatus and method for transporting a medical accessory in unison with a patient transport device such as a gurney, hospital bed or wheelchair.

Medical treatment and therapy often requires the use of several medical instruments and therapeutic devices which must be maintained in close proximity to the patient and to each other due, in part, to the limitations imposed by the length of electronic lead wires and plastic tubing. Further, if the patient is to receive uninterrupted treatment, this close proximity must be maintained not only when the patient is settled in a hospital ward, but also during transportation to and from the ward. Satisfaction of this latter requirement is especially acute for patients being moved between emergency or operating rooms and other hospital areas.

In order to satisfy the above requirements, many of the devices used for medical treatment and therapy have been mounted on intravenous infusion, or I.V., stands. For those devices where mounting on an I.V. stand has been impossible or impractical, mobility has often been achieved by placing wheels or treads directly on the equipment. Although these modifications make it possible to move almost any medical equipment as an autonomous unit, the inability to quickly and safely move a patient and their associated devices as a contiguous unit continues to make patient transportation difficult and potentially hazardous.

Several techniques are currently utilized for moving patients and their related patient care devices. These methods typically comprise: using an additional nurse, orderly, or other assistant to move the patient care device, such as an I.V. stand or other freestanding accessory, as an independent unit; rigidly connecting the stand or accessory to the transport device; or resting patient care devices directly on the patient transport device. These techniques, however, are problematic in that they rely on the presence of additional personnel or result in damaged or disorganized equipment. In addition, the weight of such devices (as much as 150 pounds) may render manual manipulation quite difficult.

Accordingly, it is a primary object of the invention to provide an apparatus which conveniently and safely couples a patient care apparatus with a patient transport device. It is a further object of the invention to provide a method for easily linking and transporting a patient care apparatus together with a patient transport device such as a bed or gurney. Yet another object of the invention is to provide a method and apparatus to facilitate the rapid and safe transport of a patient and any necessary patient care devices. These and other objects and features of the invention will be apparent from the following description of the invention and the drawings.

SUMMARY OF THE INVENTION

The present invention attains the preceding objects and features by providing a method and apparatus for transporting one or more patient care device. The apparatus of the present invention comprises a patient transport device, such as a hospital bed or gurney, a patient care device, such as an I.V. stand, and a selectively engageable coupling means for coupling the patient care device and the transport device.

According to the invention, a patient care device, such as an intravenous assembly or other diagnostic or therapeutic apparatus, may be conveniently attached to a patient transport device, such as a gurney, hospital bed, wheelchair or the like, so that the combination may be safely and easily transported as a unit. The patient transport device includes a patient platform which is supported by a frame. Preferably, the frame is vertically adjustable and has mounted thereto a first flange having at one end a means for engaging a second flange. The first flange may be vertically adjusted as a result of vertical movement of the frame. Alternatively, the first flange may be made vertically adjustable independent of the movement of the frame of the patient transport device.

The patient care apparatus, preferably has a care device, such as a fluid infusion source, mounted on an elongate vertical member having an upper portion which is detachable from a wheeled base portion. The upper portion has attached thereto a second flange which extends horizontally from the vertical member. One end of the second flange features a means for mating to the first flange. Alternatively, the vertical member of the patient care apparatus may be of a one-piece construction.

The apparatus of the present invention is used by positioning a patient care apparatus adjacent to a patient transport device such that the mating means of the first and second flanges are vertically aligned. The first flange of the patient transport device is elevated, preferably by raising the support platform, until the mating means of the first and second flange engage each other. The first flange is further elevated until the upper portion of the patient care apparatus becomes detached from the lower portion thereof, or, alternatively, until the base of the patient care apparatus is elevated off the ground. When this is done, the patient transport device and the patient care apparatus may be transported as a unit.

BRIEF DESCRIPTION OF THE DRAWINGS

FIG. 2 is a partially cutaway, side perspective view, illustrating the coupling apparatus of FIG. 1 in a coupled position;

FIG. 3 is a partially cutaway, side perspective view of the coupling apparatus of FIGURE 1 in a coupled position with the patient care apparatus disposed in a position free of its supporting base.

DETAILED DESCRIPTION

Figure 1:
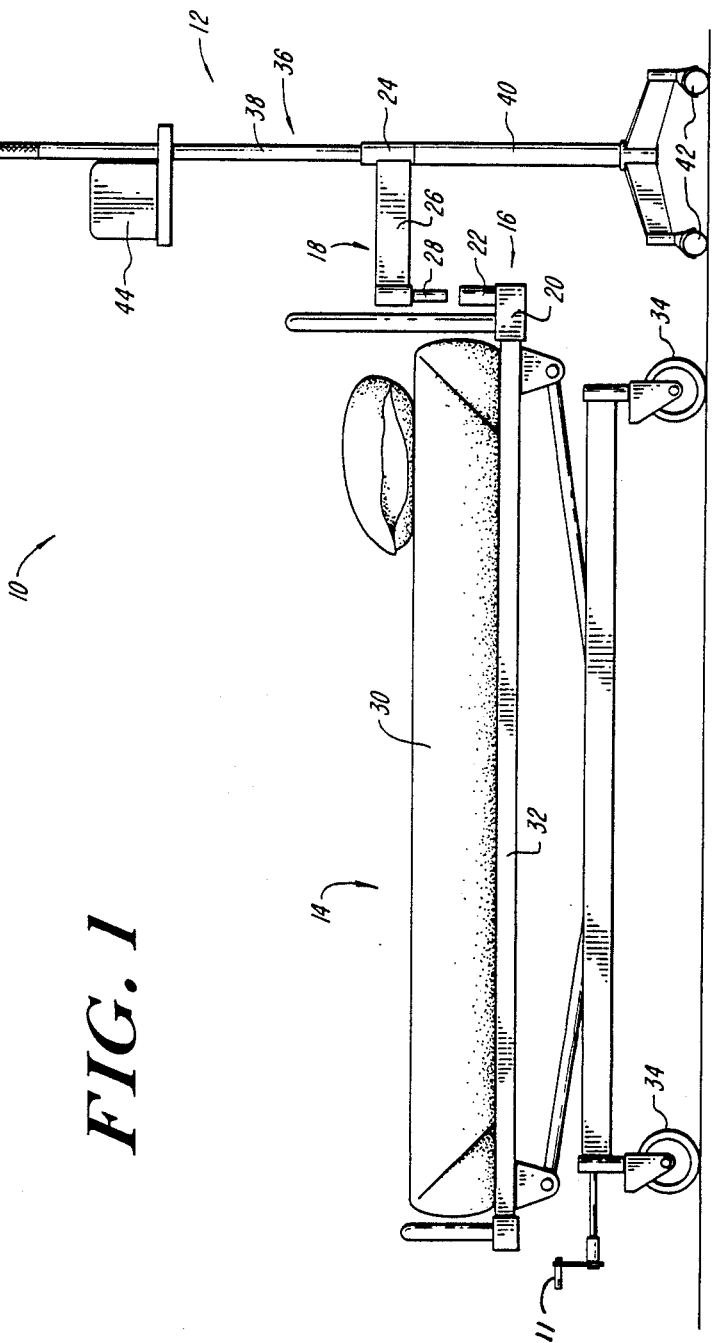
FIG. 1 is a side perspective view illustrating a patient care apparatus, a patient transport device and the coupling apparatus of the present invention in an uncoupled position.

Referring to FIGS. 1 through 3, there is illustrated a transport system 10 for a portable patient care apparatus 12. System 10 includes a patient transport device 14 having a first flange 16 affixed thereto, a patient care apparatus 12 and a second flange 18 which is attached to and extends horizontally from patient care apparatus 12.

The first flange 16 preferably includes mounting support 20 and socket means 22 for mating to the second flange 18. Likewise, the second flange 18 features a mounting support 24, horizontal flange 26, and means 28 for mating to the first flange 16.

The patient transport device 14 may be of any type suitable for use in a hospital setting, including a gurney, a hospital bed, stretcher, wheelchair or the like. Device 14 features a patient care platform 30 supported by a frame 32. Frame 32, preferably is made vertically adjustable by either a preferred automatic means (such as an electric motor, not shown), or by a manual crank 11. The frame of device 14 is preferably equipped with wheels 34 to facilitate transport.

First flange 16 is attached to the frame 32 of the patient transport apparatus 14 by a mounting 20 disposed at one end thereof. The other end of first flange 16 features socket means 22 for mating to the second flange 18. Flange 16 preferably may be vertically adjustable as a result of the vertical manipulation of frame 32. Alternatively, flange 16 may be vertically adjustable independent of frame 32 if, for example, flange 16 is mounted upon a stationary member or if the frame 32 is not vertically adjustable. Socket means 22 of first flange 16 preferably is vertically oriented and is displaced from frame 32 by a distance sufficient to allow for easy interaction with mating means 28 of second flange 18. Socket means 22 preferably is a female member of sufficient diameter and depth to securely receive and engage mating means 28.

The patient care apparatus 12 preferably comprises an assembly of intravenous infusion devices or other therapeutic or diagnostic devices. Patient care apparatus 12 includes vertical member 36, having an upper portion 38, which is detachably secured to a base portion 40. Base portion 40 may or may not be equipped with wheels 42. The upper portion 38 preferably has a means for supporting various diagnostic and therapeutic medical patient care devices 44. The base portion 40 interferringly or interlockingly engages the upper portion 38. Preferably, the base portion features a female receiving end 46 which securely engages male end 48 of the upper portion 38.

It is understood, of course, that the male and female portions described herein may be reversed. That is, base portion 40 and means 22 may feature a male member while upper portion 38 and mating means 28 may feature female elements. Moreover, the terms "vertical" and "horizontal" are used as general indicators of direction for the apparatus of the present invention while it is in its operative position. These terms should be read to include both horizontally and vertically extending members as well as members which are truly horizontal and vertical.

The second horizontal flange 18 may be secured to the lower end of upper portion 38. Flange 18 comprises a mounting support 24 which engages upper portion 38, a horizontal flange 26 and male end 28. Preferably, socket means 22 and 28 engage in such a way that upper portion 38 is able to pivot about first flange 16. However, in a preferred embodiment the range of pivot should be limited as needed in order to prevent the patient care devices 44 from becoming positioned over the patient transport device 14. It is also preferred that flange 18 be substantially longer than the overall length of the first flange 16. Additionally, flange 18 should be of sufficient strength to support upper portion 38 of the patient care apparatus 12 as well as any items disposed thereon. Generally, the load to be carried by flange 18 may be as much as 150 pounds.

Flanges 16 and 18 may be constructed of virtually any strong, durable material suitable for use in a hospital environment, such as aluminum, stainless steel or plastic.

In a preferred embodiment the patient transport apparatus 14 comprises a wheeled hospital bed with a motor capable of vertically adjusting the height of the bed. The hospital bed may be modified for use with the present invention by replacing or modifying the headboard of the bed. Preferably, a bed useful with the present invention will have a headboard which features two female sockets (i.e. first flange 16) disposed on opposite sides of a longitudinal centerline of the hospital bed. The sockets may be spaced apart by a distance of approximately 10–18 inches, and most preferably by 13 inches.

The second flange 18 useful with the preferred embodiment of the invention is attached to the upper portion 38 of an intravenous stand (i.e., patient care apparatus 12). Preferably, the second flange 18 is horizontally disposed and is approximately 7.5 inches in length from the longitudinal axis of upper portion 38 to the longitudinal axis of mating means 28.

The socket means 22 and mating means 28 are designed to securely engage each other by a frictional fit in order to effectively support the patient care device. The dimensions of female socket 22 and male member 28 are not necessarily critical and may be easily designed by one of ordinary skill in the art. Preferably, however, male member 28 has a slightly stepped diameter. The top portion of member 28 is preferably about 1.0 inch in diameter while the midportion of member 28 has a diameter of 0.875 inches. The diameter of the bottom portion of member 28, however, again increases to about 0.937 inches. Additionally, the extreme upper tip of member 28 is tapered over approximately 30° to facilitate insertion within socket 22. The length of member 28 is approximately 4.75 inches.

Socket 22 is slightly larger in diameter than member 28. Preferably, the opening of socket 22 is 1.01 inches. The diameter of socket 22 is stepped, so that corresponding sections of the socket 22 are slightly greater in diameter than member 28. For example, the bottom portion of socket 22 has a diameter of approximately 0.940 inches.

It is noted that the above design and dimensions represent only the currently preferred embodiment of the invention. It is expected that aspects of the design and certain dimensions may be modified by one of ordinary skill in the art without departing from the spirit and scope of the invention. For example, although the invention is described with respect to first flange 16 being capable of vertical adjustment, it is understood that second flange 18 may, alternatively, be adapted for vertical adjustment by means of a motor or cranking device (not shown).

FIGS. 1 through 3 illustrate, in sequence, the manner in which the present invention may be used. First flange 16 is secured to the frame 32 of patient transport apparatus 14. Preferably, flange 16 is positioned at the head of patient transport apparatus 14. A second flange 18 is disposed on the upper portion 38 of patient care apparatus 12. The patient care apparatus 12 is moved into a position adjacent the first flange 16 of the patient care apparatus 14. Preferably, the second flange 18 is aligned such that it is disposed directly above first flange 16, as shown in FIG. 1. The first flange 16 is then elevated by raising the frame 32 of the patient transport apparatus 14. Flange 16 is elevated until the socket 22 and mating means 28 of the first and second flanges 16, 18 engage as shown in FIG. 2. The first flange 16 is further elevated until upper portion 38 of the patient care apparatus 12 becomes detached from the base portion 40 thereof, as shown in FIG. 3. At this point, the patient transport apparatus 14 and the attached patient care apparatus 12 may be transported as a unit without interrupting the functioning of any diagnostic or therapeutic equipment.

Although particular embodiments of this invention have been described and illustrated herein, it is recognized that modifications and variations may readily occur to those skilled in the art. Consequently, it is intended that the claims be interpreted to cover such modifications and the equivalents.

What is claimed is:

1. An apparatus for transporting a patient care device, comprising:
   a patient transport device having a frame supporting a patient care platform;
   a first horizontal flange secured to the patient transport device, said first horizontal flange having disposed on one end thereof a means for mating to a second horizontal flange;
   a freestanding patient care apparatus having an elongate vertical member adapted for supporting a patient care device;
   a second horizontal flange extending from the vertical member, said second horizontal flange having disposed on one end thereof a means for mating to said first horizontal flange; and
   means for vertically adjusting at least one of said flanges to matingly engage said mating means of said flanges and to suspend the patient care device from the first flange.

2. The apparatus of claim 1, wherein the elongate member has an upper portion and a lower portion and the upper portion is detachable from the lower portion thereof.

3. The apparatus of claim 2, wherein at least a portion of the frame of the patient transport device is vertically adjustable.

4. The apparatus of claim 3, wherein the first horizontal flange is secured to the frame of the patient transport device.

5. The apparatus of claim 4, wherein said first horizontal flange is vertically adjustable as a result of the vertical adjustment of the patient transport device.

6. The apparatus of claim 4, wherein said first horizontal flange is vertically adjustable independent of the vertical adjustment of the patient transport device.

7. The apparatus of claim 4, wherein the second horizontal flange is secured to the upper portion of the vertical member.

8. The apparatus of claim 1, wherein said patient transport device is a gurney.

9. The apparatus of claim 1, wherein said patient transport device is a wheelchair.

10. The apparatus of claim 7, wherein the mating means of the first horizontal flange interlockingly engages the mating means of the second horizontal flange such that upon vertical elevation of the first horizontal flange the upper portion of the vertical member becomes detached from the lower portion thereof, enabling the patient care device to be securely mounted to the patient transport device.

11. The apparatus of claim 10, wherein the mating means of the first horizontal flange comprises a female member.

12. The apparatus of claim 11, wherein the mating means of the second horizontal flange comprises a male member.

13. The apparatus of claim 12, wherein the second horizontal flange is substantially longer than the first horizontal flange.

14. The apparatus of claim 1, wherein the patient care device comprises an intravenous apparatus.

15. A method of securing a patient care device to a patient transport device for unitary transport thereof, comprising the steps of:
    providing a patient transport device having affixed thereto a first horizontal flange, one end of which comprises a means for mating to another flange;
    providing a patient care apparatus having a vertical member supporting a patient care device, said vertical member having an upper portion which includes a protruding second horizontal flange having at one end thereof a means for mating to the first horizontal flange;
    aligning the mating means of the first horizontal flange directly below the mating means of the second horizontal flange;
    elevating the first horizontal flange such that it interlockingly engages the second horizontal flange; and
    continuing to elevate the patient transport device so that the upper portion of the vertical member detaches from the lower portion thereof to become freely supported by the patient transport device.

16. The apparatus of claim 1 wherein the first horizontal flange is vertically adjustable.

17. The apparatus of claim 16 wherein the vertical adjustment of the first flange is dependent on the adjustment of the patient transport device.

18. The apparatus of claim 1 wherein the second horizontal flange is vertically adjustable.

19. The apparatus of claim 18 wherein the vertical adjustment of the second horizontal flange is dependent on the vertical adjustment of a portion of the patient care apparatus.

20. The apparatus of claim 1 wherein the mating means of the first and second flanges mate in pivotal engagement.

* * * * *